(12) United States Patent
Schneider et al.

(10) Patent No.: US 10,883,752 B1
(45) Date of Patent: Jan. 5, 2021

(54) FAN DRIVEN THERMAL TREATMENT DEVICE

(71) Applicants: Chase Schneider, Orlando, FL (US); Cole Schneider, Orlando, FL (US)

(72) Inventors: Chase Schneider, Orlando, FL (US); Cole Schneider, Orlando, FL (US)

( * ) Notice: Subject to any disclaimer, the term of this patent is extended or adjusted under 35 U.S.C. 154(b) by 155 days.

(21) Appl. No.: 16/056,542

(22) Filed: Aug. 7, 2018

Related U.S. Application Data (60) Provisional application No. 62/605,497, filed on Aug. 16, 2017, provisional application No. 62/605,496, filed on Aug. 16, 2017.

(51) Int. Cl.
*F25D 3/08* (2006.01)
*F04D 29/60* (2006.01)
*F04D 25/08* (2006.01)

(52) U.S. Cl.
CPC ............... *F25D 3/08* (2013.01); *F04D 25/08* (2013.01); *F04D 29/601* (2013.01)

(58) Field of Classification Search
CPC ... F25D 3/08; F25D 23/12; F25D 5/00; F04D 29/601; F04D 25/08
USPC ........................................................ 62/259.3
See application file for complete search history.

(56) References Cited

U.S. PATENT DOCUMENTS

| | | | |
|---|---|---|---|
| 4,744,106 A | * | 5/1988 | Wang ..................... A42B 3/286 2/171.3 |
| 5,088,549 A | | 2/1992 | Schneider |
| 8,771,331 B2 | | 7/2014 | Geibel |
| 9,644,880 B2 | | 5/2017 | Paul |
| 2007/0225783 A1 | | 9/2007 | Koby et al. |
| 2009/0036960 A1 | | 2/2009 | Blair |
| 2011/0042426 A1 | | 2/2011 | Liang |

FOREIGN PATENT DOCUMENTS

WO   WO-2016135529 A1 * 9/2016 ............. A42B 3/286

* cited by examiner

*Primary Examiner* — Ana M Vazquez
(74) *Attorney, Agent, or Firm* — Stan Collier, Esq.

(57) ABSTRACT

The thermal treatment device is primarily to be wrapped about one's neck. The thermal treatment device is an elongated container, like a sleeve, having two sides that may be air permeable. The container has one or more aligned pockets capable of holding gel packs. A source of power is placed in one pocket of the container and has on-off switch. Also included is a microfan device being placed in a pocket and receiving power from the source of power. The microfan device has air outlet and air inlet openings thereabout. The microfan blades are positioned between a top row of air inlet holes and a bottom row of air outlet holes. The microfan blows air into the gel pack pockets past the cooled gel packs and then exits through the one or more air permeable sides to cool the user. The gel packs may be removable.

7 Claims, 7 Drawing Sheets

FAN DRIVEN THERMAL TREATMENT DEVICE

CROSS REFERENCES TO RELATED APPLICATIONS

The present utility application claims priority to provisional patent application Ser. No. 62/605,496, filed Aug. 16, 2017, entitled, "Fan Module for Treating Air Within Enclosures", by inventors Chase and Cole Schneider, and provisional patent application Ser. No. 62/605,497, filed Aug. 16, 2017, entitled, "Fan Driven Thermal Treatment Device", by the same inventors.

Reference to Federally sponsored research or development: NA

Reference to joint research agreements: NA

Reference to Sequence Listing: NA

BACKGROUND OF THE INVENTION

Field of the Invention

The present invention relates generally to bodily comfort, and, in particular, to devices providing cooling air, and, in great particularity, to devices providing forced cooling air by fan to a user and to a particular body location.

Description of the Prior Art

Being comfortable in hot and humid weather is always desired by the consumer. In some environments air conditioning can be used at home or in a car, but this is not always available.

Many inventions are directed at providing a source of cooling air or placing a cold object against the body. U.S. Patent Application Publication 2007/0225783 shows an elongated fabric envelope with end ties. A thermal pack can be placed inside of the envelope. U.S. Patent Application Publication 2009/0036960 discloses an ice wrap having end ties. U.S. Patent Application Publication 2011/0042426 discloses a flexible band to go about the upper body, i.e., neck with a bottle holder that will hold a cooled bottle to the back of the neck. U.S. Pat. No. 5,008,549 discloses a neckband for holding cooling pouches. A zippered entrance allows for the neckband to be filled with ice and to be used like a neck scarf. U.S. Pat. No. 8,771,331 shows a wrap with a coolable liquid therein having wings on the ends. U.S. Pat. No. 9,644,880 shows an elongated body member with a compartmented container. All prior art is incorporated by reference.

Accordingly, there is a need for a device and method of providing a source of cooling for use on a body part.

SUMMARY OF THE INVENTION

The thermal treatment device is primarily to be wrapped about one's neck. The thermal treatment device is an elongated flexible container having one or more sides that are air permeable. The container has one or more pockets capable of holding gel packs. A source of power is placed in a pocket of the container and has on-off switch. The batteries are rechargeable. Also included is a microfan device being placed in a pocket and receiving power from the source of power. The microfan device has a housing with air outlet and air inlet openings thereabout. The fan blades are positioned between a top row of air inlet holes and a bottom row of air outlet holes. The microfan blows air into the gel pack pockets past the cooled gel packs and then exits through the one or more air permeable sides to cool the user. The gel packs are removable.

A microfan device of the present invention can be placed in almost any container and is used in the thermal treatment device. The housing of the microfan is a cylinder with a top aperture and a screen-like cover over the aperture. The bottom is a solid surface. The cylindrical wall of the housing has air outlet and air inlet openings thereabout. A multi-bladed fan is battery operated and can be removed or replaced. The fan blades are positioned between a top row of air inlet holes and a bottom row of air outlet holes. The fan blades fit closely within the cylindrical wall to insure movement of air therethrough. From a horizontal view, the blades are located between the outlet and inlet holes. Materials may be added to the housing or blades to provide a deodorant or other material.

It is an object of the present invention to provide a container being a thermal treatment device having a forced air source to output cool air added by cooled gel packs therein;

It is another object of the present invention to provide a thermal treatment device that can be easily applied to different parts of the body;

It is a further object of the present invention to provide a thermal treatment device that can be reused;

It is still a further object of the present invention to provide a thermal treatment device that can be operated by rechargeable batteries;

It is still another object of the present invention to provide a thermal treatment device having removable gel packs that can be independently cooled;

It is still another object of the present invention to provide a thermal treatment device having a cooled surface and further output cooled air;

It is still another object of the present invention is to provide a thermal treatment device having a microfan device therein to move air therein; and These and other objects, features, and advantages of the present invention will become more readily apparent from the attached drawings and the detailed description of the preferred embodiments, which follow.

BRIEF DESCRIPTION OF THE DRAWINGS

Like reference numerals refer to like parts throughout the several views of the drawings.

DETAILED DESCRIPTION OF THE PREFERRED EMBODIMENTS

The thermal treatment device of the present invention is primarily to be wrapped about one's neck for its cooling effect. The thermal treatment device is an elongated flexible container having one or more sides that are air permeable. The container has one or more pockets capable of holding gel packs. A source of power is placed in a pocket of the container and has on-off switch. The batteries are rechargeable. Also included is a microfan being placed in a pocket and receiving power from the source of power. The on-off switch controls the fan. The fan blows air into the gel pack pockets past the cooled gel packs and then exits through the one or more air permeable sides to cool the user. The device is approximately 2 inches wide and about 2 feet long. The sides of the container are attached together on their edges and the container is capable of being wrapped about a neck. To further secure the device, ties may be included to secure a first end of said container to a second end of said container. The gel pack pockets are parallel to the length and have a closeable opening for inserting the gel packs.

Figure 7A:
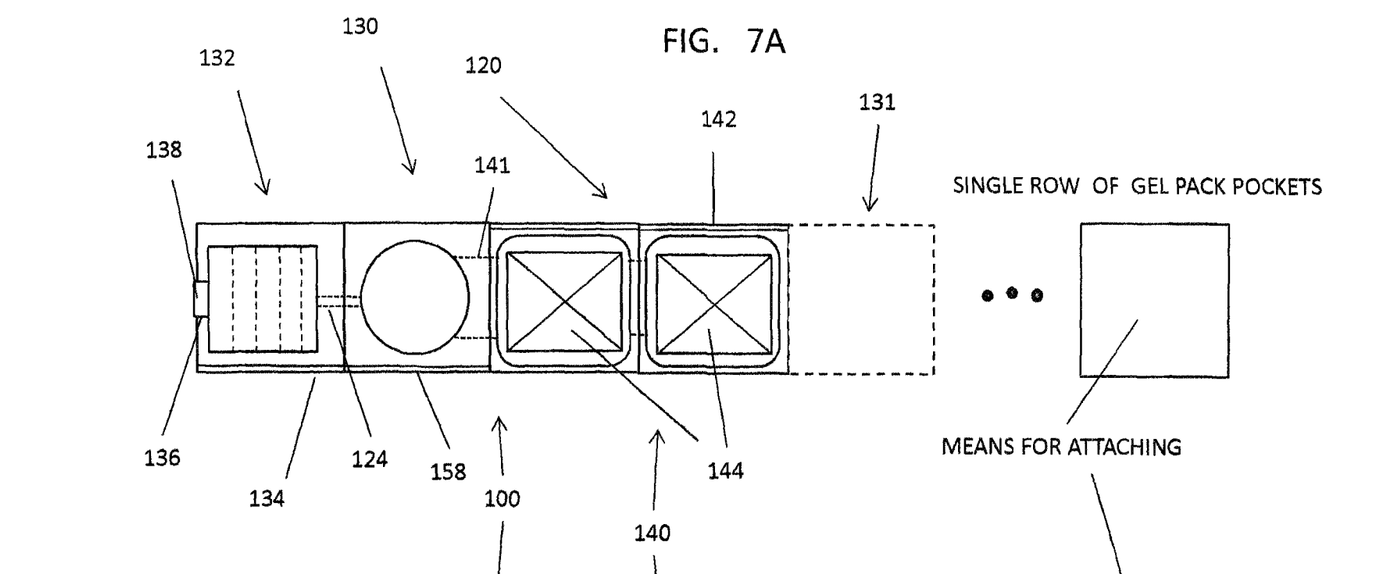
FIGS. 7A and 7B are top views of the microfan driven thermal treatment device with two embodiments.
Figure 7B:
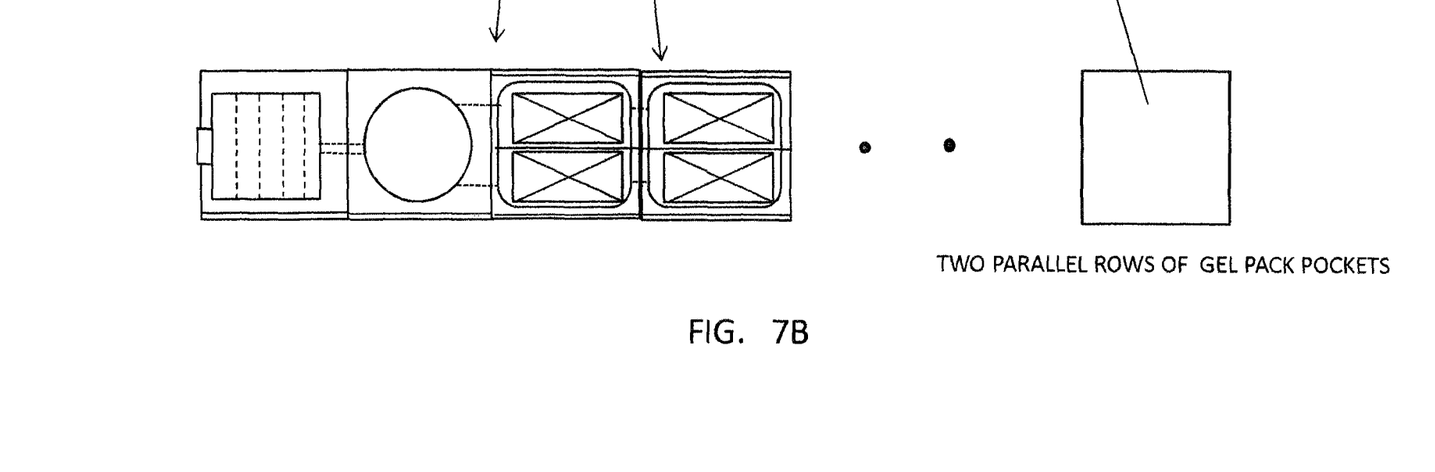
Figure 8:
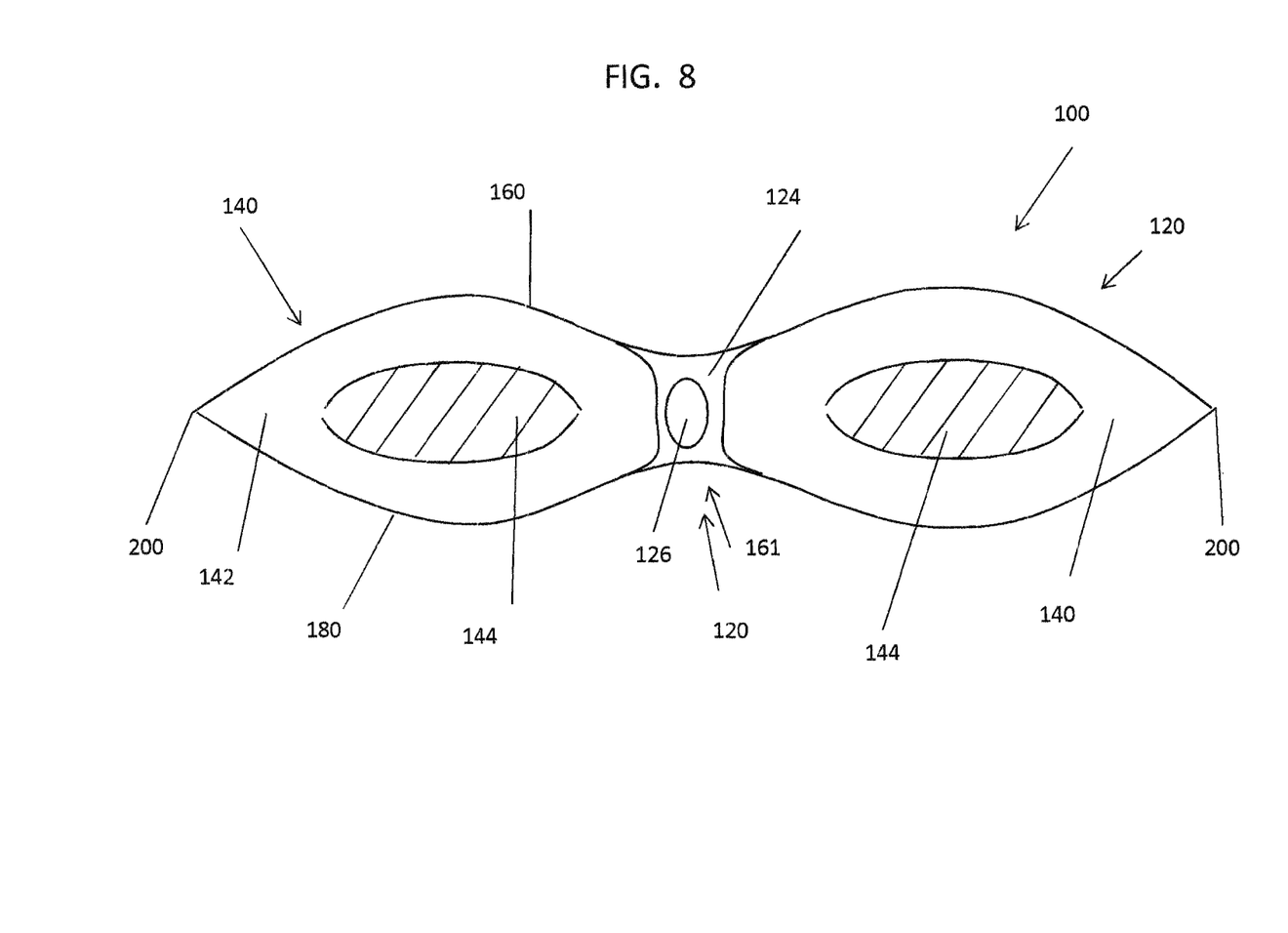
FIG. 8 is a cross sectional view through the microfan driven thermal treatment device of FIG. 7A.

In a preferred embodiment, referring to FIGS. 7A and 7B and 8 and 9, a thermal treatment device 100 is shown by top view in FIG. 7A or 78. The device 100 is an elongated flexible container 120 having flexible fabric-like side walls 140, a top wall 160 and a bottom wall 180, that are permanently attached at the outer edges 200 and in the center 120 if there are two rows such as shown in FIG. 7B. The container 120 is shaped like an envelope and may have a thickness of about ½ to 1 inch. If a microfan section 130 is not adjacent to a battery housing section 132, a wire tunnel 124 with wires 126 therein runs from a source of power 132 being rechargeable batteries, for example, inserted into a battery housing section 132 having a zipper 134, FIG. 7A, or the like for closing the entrance after the insertion of the batteries. The zipper 134 can be replaced by other conventional devices such as hook and loop connectors. An on-off switch 136 and/or an indicator on-light as well as a battery charging port 138 are in the battery housing section 132.

The elongated air permeable container 120 has multiple pockets 140 capable of holding multiple gel packs 144 one or more attached together. In one embodiment, the bottom wall 180, FIG. 8, may not be air permeable since this wall will be in direct contact with the skin and little if any air would be able to flow therethrough, and thus the top wall 160 would be air permeable and may be further aided by multiple small holes therein, not shown. In another embodiment, both top and bottom walls 160 and 180 would be air permeable. The walls 160 and 180 may be composed of fabric or plastic matter or a combination of both and further may have added holes therein or be mesh-like and being air permeable. In FIG. 7A, the pockets being in a single row are attached together and further allow air to flow from one pocket to the next. A means for attaching at the end of device 100 may be ties or Velcro or similar means for holding the device 100 about one's neck. The microfan section 130 may also be placed in the center of the pockets. Air would thus flow in two different directions.

Figure 9:
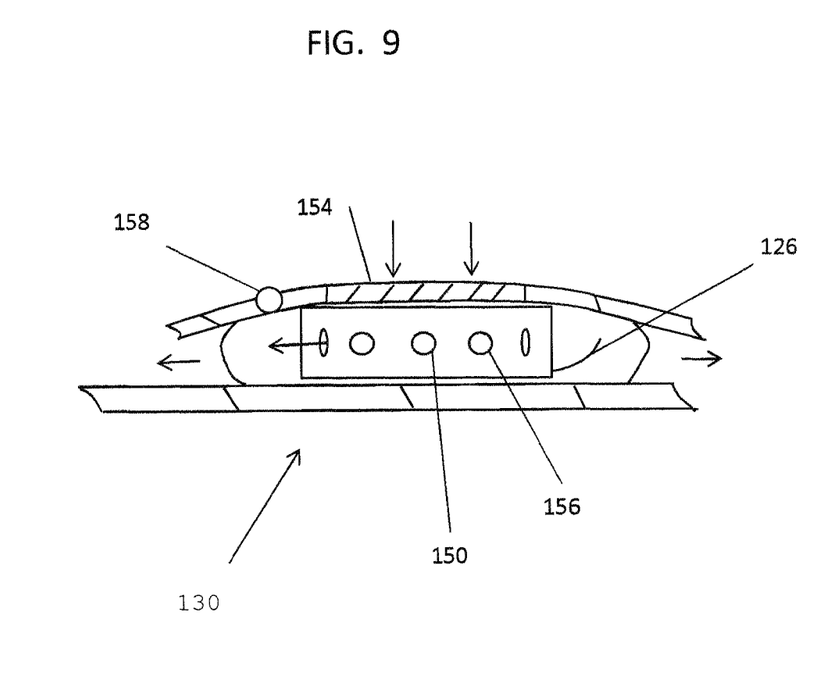
FIG. 9 illustrates a microfan in a pocket of the microfan driven thermal treatment device of FIG. 7A or FIG. 7B.

FIG. 9 illustrates by cross sectional view a microfan 150 in a fan pocket 130 which has a mesh opening 154 in the fan pocket 130 to allow air, shown by arrows, to enter therein. The fan 150 will blow the air therefrom through a series of air outlets 156 or the like that will allow the air to enter into gel pack pockets 140 and 142 past the cooled gel packs 144 and through the walls. A zipper 158 in the fan pocket 130 will allow the fan 150 to be removed as necessary. The fan pocket 130 will typically be located in the middle of the device 100 or at one end as shown. A plurality of zippers 160 on the pockets 140 and 142 will allow the gel packs 144 to be inserted into and removed.

The container 120 in this embodiment will be approximately 2 inches wide and about 2 feet long, and is capable of being wrapped about a neck. Although not shown, means for securing a first end of said container to a second end of said container such as ties may be included.

Figure 1:
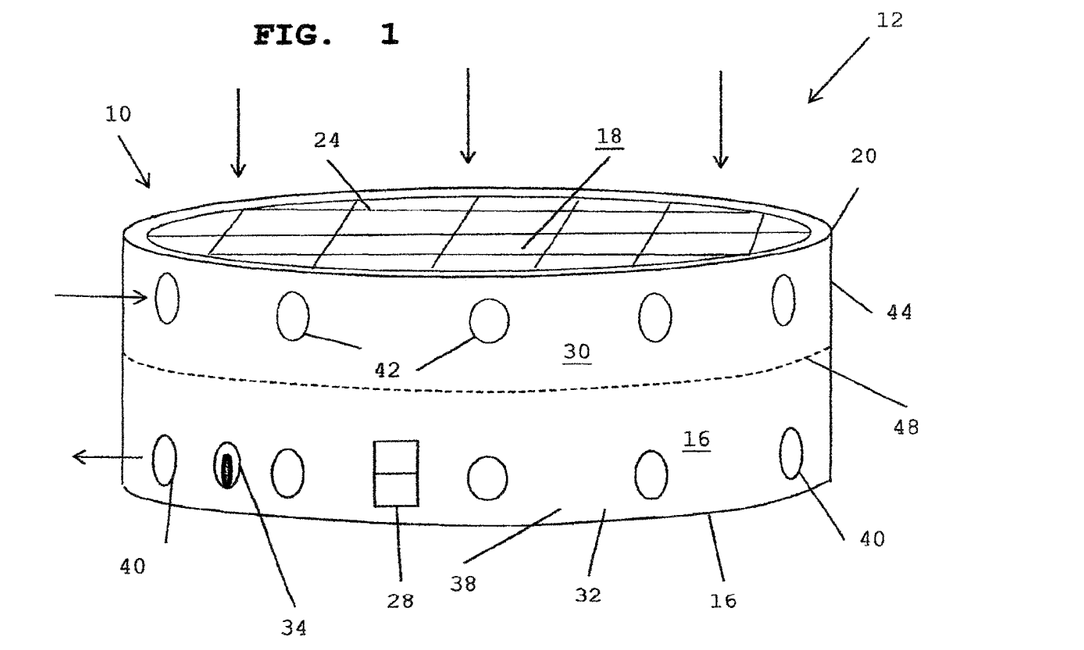
FIG. 1 is a top view a microfan module of the present invention.
Figure 2:
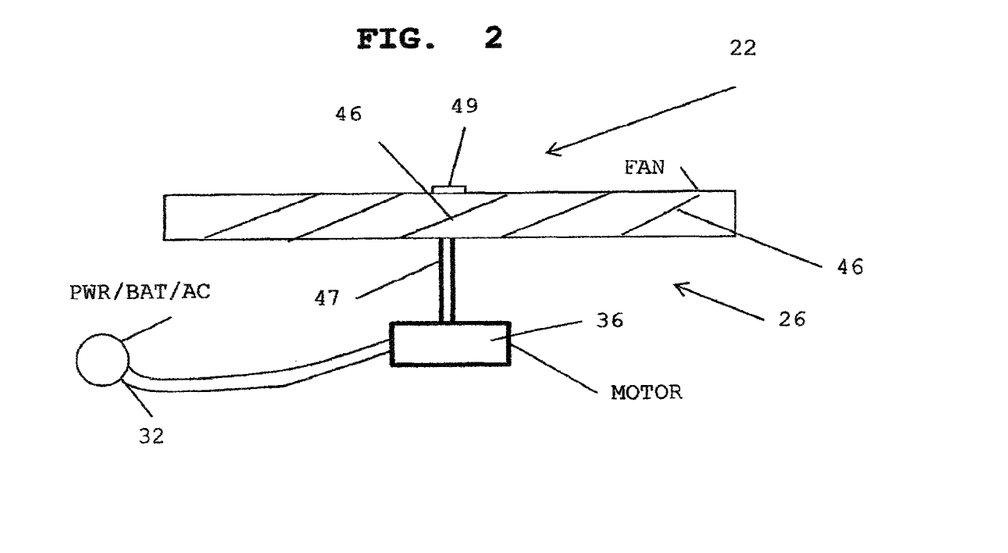
FIG. 2 is a side view of the microfan of the Present invention as shown in FIG. 1.
Figure 3:
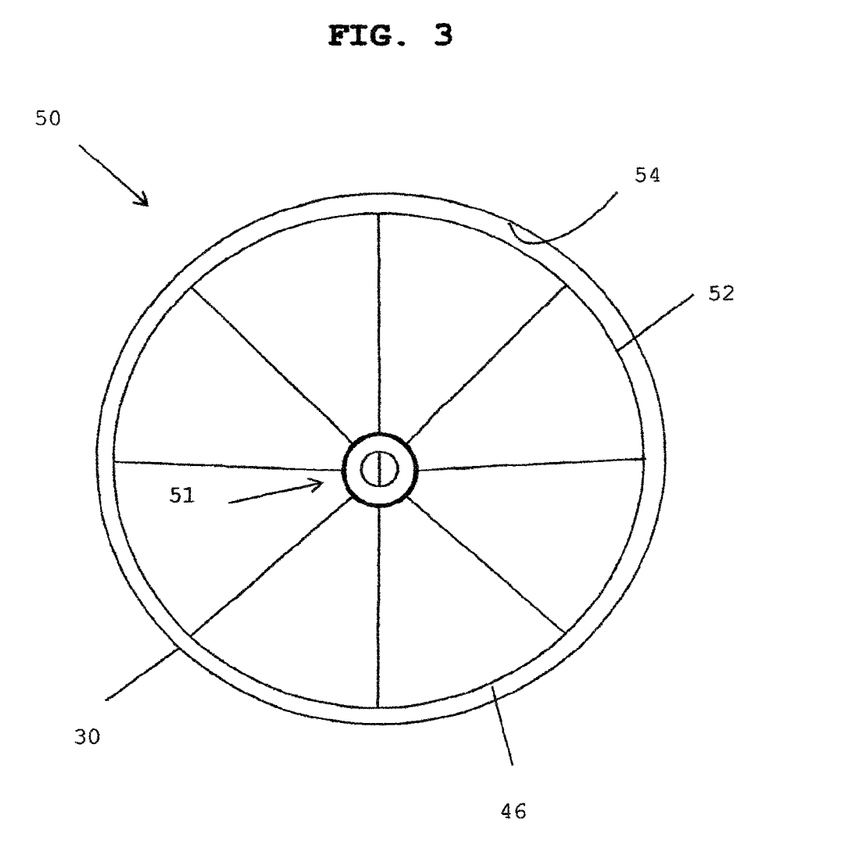
FIG. 3 is a top view of a fan blade of the present invention.
Figure 4:
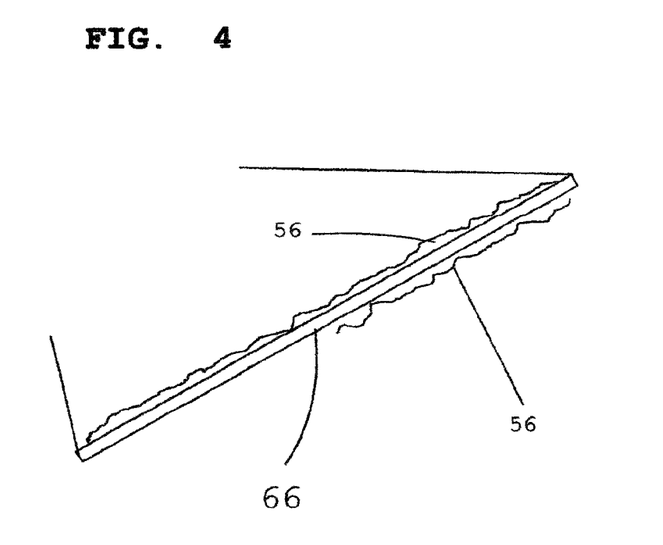
FIG. 4 is a sectional view of a partial section of the microfan module housing of the present invention.
Figure 6:
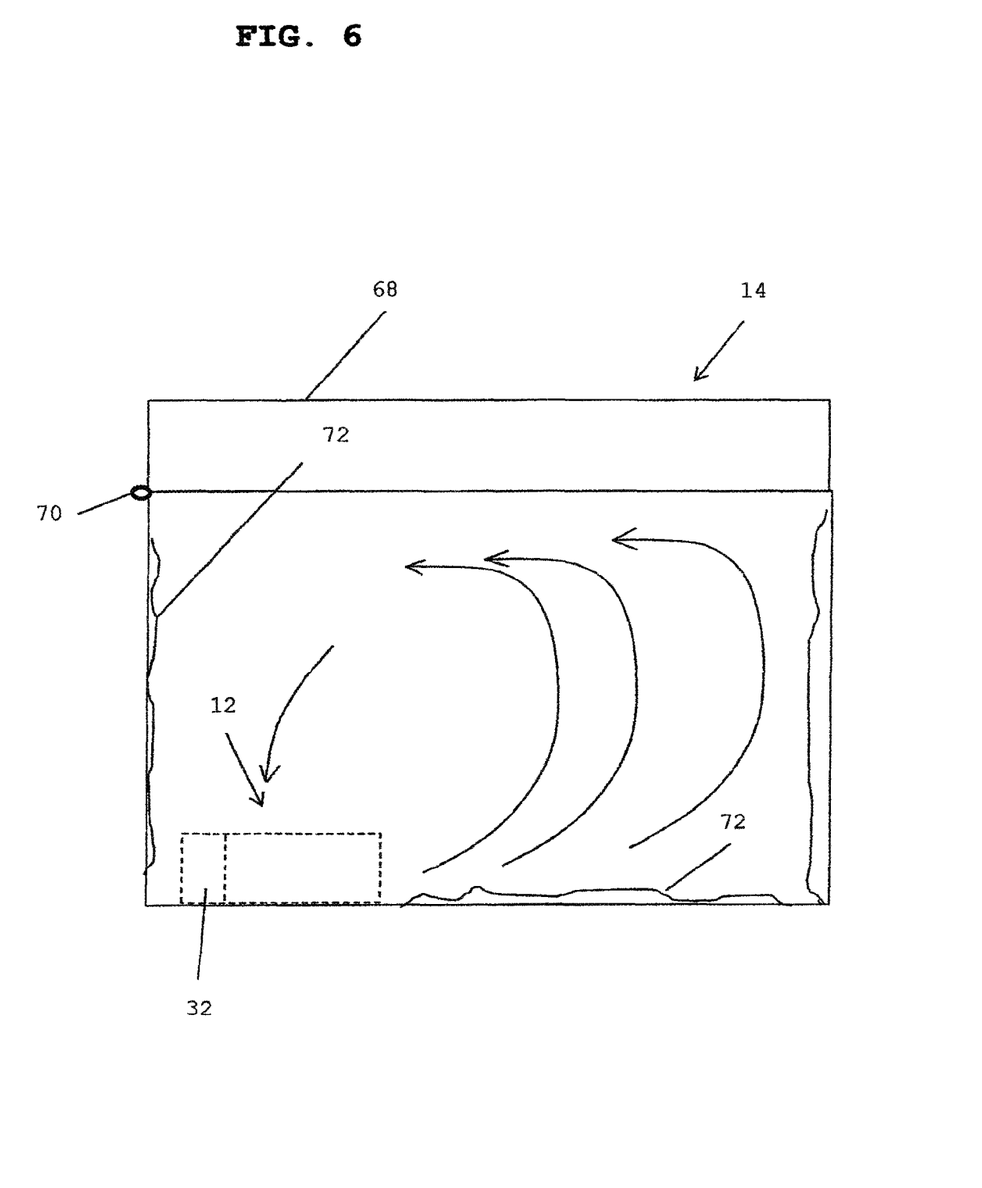
FIG. 6 is a side view of a container including one or more microfan modules therein.

Referring to FIG. 1, a portable air treatment device 10 is shown being a microfan module 12 for moving air in many possible containers such as removing tarnishing materials from a jewelry box, odors, or the placement of deodorants from/in enclosures in containers where these container may be a jewelry case or box, a luggage, a gym bag, a locker, a closet, or a cooling device as discussed herein. The container 14, FIG. 6, is a jewelry case, but may be any container as noted above. The microfan module 12 has a cylindrically shaped housing 16, FIG. 1, with an aperture 18 in a top side 20 of the housing 16. A fan 22, FIG. 2, is located inside of the housing 16. A screen or filter with or without tarnish removing material 24 is further located in the aperture 18 to prevent any object from hitting the fan blades 26. An on-off switch 28 may be on the housing wall 30 as well as an indicator on-light or in a close location such as in a pocket of flexible material. A battery pack 32 may be located in the housing or may be on the outside of the housing 16 or in a battery pocket of flexible material. A power inlet 34 may be used to power the fan motor 36 and other modules 12 in the container 14 via battery that may be rechargeable, or an AC/DC converter. About the lower edge 38 of the wall 30 are a series of air outlet openings or holes 40. Additionally, as desired, air inlet openings or holes 42 may be located about an upper edge 44 of the wall 30 to prevent choking when the module is flipped over. This will aid in air flow if the module 12 is flipped over onto the aperture 18. The fan blades outer edges 46 are in close proximity to the inside of the wall 30 so that air is efficiently moved therethrough. The outer edges 46 travel horizontally in FIG. 1 along the dotted line 48. A preferred embodiment of the fan blades 50 are shown in FIG. 3 where there are multiple blades that may cover almost entirely the inside of the housing. The outer edges 52 are in close proximity to the inside wall 54. Further the number of blades 50 may be 4 or more and may be slanted at a low angle to increase the available surface area where the tarnish removing material or odor prevention material or deodorant or a combination of one or more of such 56 is coated. Further it may be coated on both sides of the blades. Further the blades may be removable to replace or refresh the materials thereon by unscrewing the housing 16 or the like along the line 48. The fan shaft 47, FIG. 2, may be keyed 51 to the blades 50, FIG. 3, and secured thereon by screwing or a nut 49, FIG. 2.

Figure 5:
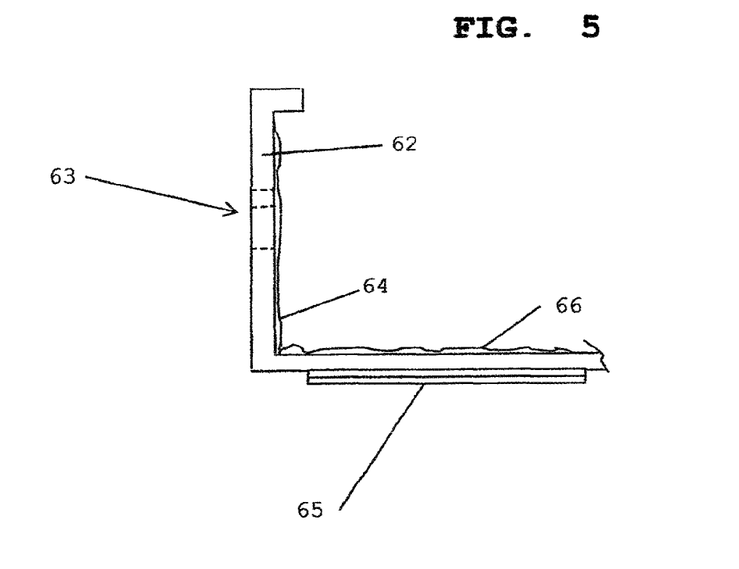
FIG. 5 is a sectional view of a partial cross section of the microfan module housing of the present invention.

The fan module 12, partially shown in FIG. 5, may further include on the inside wall 62 of the housing 16 a coating 64 thereon or a flexible fabric 66 for the tarnish removing material, odor prevention material, or a deodorant material thereon as well as on a solid bottom wall/floor 66 as shown in FIG. 5. FIG. 5 also shows a means for attaching 65 the module 12 to another surface by, for example, a peel and sticker, a hook and loop, or even a hook into hook opening 63. FIG. 6 shows the container 14 having one fan module 12 therein. Air flow is shown by arrows. The container 14 may have a lid 68 hinged by hinge 70 to the lower box 72. The inside of the container 14 may also include tarnish removing cloth 72 or other materials as mentioned herein.

Since many modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A device for providing thermal treatment to a human body, said device comprising:
   an elongated, flexible, air permeable container, said container having one or more pockets capable of holding gel packs, said container being shaped-like an envelope having two sides, one or more sides are air permeable;
   a source of power, said source of power being placed in said container, said source of power having an on-off switch, an indicator on-light, and a rechargeable port; and
   a microfan module, said microfan module having a cylindrical housing with a top aperture for air inlet, said housing having air inlets and air outlet openings thereabout, said microfan module being placed in a pocket and receiving power from said source of power, said microfan module connected to said source of power through said on-off switch, said microfan module being capable of blowing air into said one or more pockets past cooled gel packs therein, and said blowing air exiting to cool the human body.

2. The device for providing thermal treatment as defined in claim 1, wherein said container is approximately 2 inches wide and about 2 feet long, and being capable of being wrapped about a neck of a human body.

3. The device for providing thermal treatment as defined in claim 1, wherein said one or more pockets for gel packs being at least two pockets for cooling sources, said two pockets being parallel to a length of said container.

4. The device for providing thermal treatment as defined in claim 1, wherein said microfan module is capable of blowing air into said pockets, and said blown air escaping therefrom through said one or more air permeable sides of said pockets.

5. The microfan module as defined in claim 1, said housing further including having a power inlet.

6. A device for providing thermal treatment to a human body, said device comprising:
   an elongated, flexible, air permeable container, said container having one or more pockets capable of holding gel packs, said container being shaped-like an envelope;
   a source of power, said source of power being placed in a pocket of said container, said source of power having an on-off switch, an indicator on-light, and a rechargeable port; and
   a microfan module, said microfan module being placed in a pocket and receiving power from said source of power, said microfan module connected to said source of power through an on-off switch, said microfan module being capable of blowing air into one or more pockets past gel packs therein, and said blowing air exiting to cool the human body when the gel packs are cooled; said microfan module comprising:
   a cylindrically shaped microfan module having a housing, said housing having an aperture in a top side, and said on-off switch on said housing;
   a microfan located in said housing, said microfan having blades; and
   air treatment material, said air treatment material being located in one or more pockets.

7. The device for providing air treatment as defined in claim 6 further including one or more gel packs as said air treatment material in said one or more pockets for cooling.

* * * * *